US006466309B1

(12) United States Patent
Kossakovski et al.

(10) Patent No.: US 6,466,309 B1
(45) Date of Patent: Oct. 15, 2002

(54) METHOD AND APPARATUS FOR CHEMICAL AND TOPOGRAPHICAL MICROANALYSIS

(75) Inventors: Dmitri A. Kossakovski, Pasadena, CA (US); John D. Baldeschwieler, Pasadena, CA (US); Jesse L. Beauchamp, La Canada, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/511,616

(22) Filed: Feb. 22, 2000

Related U.S. Application Data

(60) Provisional application No. 60/121,860, filed on Feb. 26, 1999.

(51) Int. Cl.[7] .......................... G01B 11/24; G01N 21/63
(52) U.S. Cl. .......................................... 356/73; 356/318
(58) Field of Search .................... 356/73, 317, 318, 356/72

(56) References Cited

U.S. PATENT DOCUMENTS 5,479,024 A  * 12/1995  Hillner et al. ............ 250/458.1
6,002,471 A  * 12/1999  Quake ........................ 356/73

OTHER PUBLICATIONS

Kossakovski et al, Ultramicroscopy, vol. 71, 1998, pp. 111–115.*

* cited by examiner

Primary Examiner—F. L. Evans
(74) Attorney, Agent, or Firm—Daniel L. Dawes; Myers, Dawes & Andras LLP

(57) ABSTRACT

A scanning probe microscope is combined with a laser induced breakdown spectrometer to provide spatially resolved chemical analysis of the surface correlated with the surface topography. Topographical analysis is achieved by scanning a sharp probe across the sample at constant distance from the surface. Chemical analysis is achieved by the means of laser induced breakdown spectroscopy by delivering pulsed laser radiation to the sample surface through the same sharp probe, and consequent collection and analysis of emission spectra from plasma generated on the sample by the laser radiation. The method comprises performing microtopographical analysis of the sample with a scanning probe, selecting a scanned topological site on the sample, generating a plasma plume at the selected scanned topological site, and measuring a spectrum of optical emission from the plasma at the selected scanned topological site. The apparatus comprises a scanning probe, a pulsed laser optically coupled to the probe, an optical spectrometer, and a controller coupled to the scanner, laser and spectrometer for controlling the operation of the scanner, laser and spectrometer. The probe and scanner are used for topographical profiling the sample. The probe is also used for laser radiation delivery to the sample for generating a plasma plume from the sample. Optical emission from the plasma plume is collected and delivered to the optical spectrometer so that analysis of emission spectrum by the optical spectrometer allows for identification of chemical composition of the sample at user selected sites.

21 Claims, 11 Drawing Sheets

METHOD AND APPARATUS FOR CHEMICAL AND TOPOGRAPHICAL MICROANALYSIS

RELATED APPLICATIONS

The present application is related to U.S. Provisional Patent Application serial no. 60/121,860, filed Feb. 26, 1999.

The U.S. Government has certain rights in this invention pursuant to Grant No. NAG5-7081 awarded by NASA.

BACKGROUND OF THE INVENTION

1. Field Of The Invention

The present invention relates generally to the field of surface chemical and topographical analysis. Specifically, the present invention includes a method and apparatus for analyzing the surface of a material using a combination of a scanning probe microscope (SPM) and laser induced breakdown spectroscopy (LIBS).

2. Description of the Prior Art

Imaging of chemically inhomogeneous surfaces is a common analytical task. Depending on the nature of the sample, the characteristic size of analyzed features, and the type of information required, various methods are employed. The majority of currently available commercial instrumentation utilizes particle beams originating from a remote source to probe the local chemical environment on the sample. Particles in the beam can be electrons (electron microscopy, Auger microprobes), ions (secondary ion mass spectrometry), X-ray photons (X-ray fluorescence) and other sources. A review of these well established techniques is described by Vickerman, "Surface Analysis: the Principal Techniques," Chichester, N.Y., John Wiley (1997). Laser microanalysis methods are reviewed by Moenke-Blankenburg, "Laser Microanalysis," Chichester, N.Y., John Wiley (1989).

The last decade has seen a rapid rise of scanning probe microscopy, SPM, as a prominent and versatile approach for surface studies. SPM instruments are differentiated from the beam-based ones by the fact that they use solid proximal probes for localized analysis. The most commonly used SPM methodology is atomic force microscopy, AFM. In its basic implementation, AFM provides topographical information with nanometer resolution. The most common modifications of AFM allow the magnetic, electrostatic, and specific chemical environment to be examined. See, Takano et.al., "Chemical and Biochemical Analysis Using Scanning Force Microscopy," Chemical Reviews 99 (1999) 2845–2890. All of the AFM methods described are indirect or measure a variable other than the measured parameter, but which has some type of dependence on the parameter to be measured. However, there is no direct way today to perform general chemical analysis with AFM probes.

Near-field scanning optical microscopy, NSOM, is another variation of SPM where sharp tapered optical probes, such as fibers or micro pipettes, serve dual purposes, being proximal probes of sample topography, and providing the means for localized light delivery for optical studies with sub-wavelength spatial resolutions. Again, NSOM itself does not have a general chemical contrast capability. However, the capability to deliver light to localized area opens the way to a multitude of experiments that can be devised using different aspects of light interaction with the sample.

One approach in this family of light-based methods is laser induced breakdown spectroscopy, LIBS. LIBS is widely used to study elemental composition of samples by analyzing optical emissions from pulsed plasmas created by a focused laser beam. It was pioneered by Radziemski in the early eighties. See, Radziemski Anal. Chem., 55 (1983) 1246–2486. Other names which are sometimes used to describe essentially the same technique are laser induced plasma spectroscopy (LIPS) and laser spark spectroscopy (LASS). Song and co-authors have recently published a review of LIBS applications. See Song, et.al., Appl. Spec. Rev. 32 (1997) 183–235.

It is an object of the present invention to provide a method and apparatus for simultaneous topographical and chemical analysis with high spatial resolution.

Another object of the present invention is to provide a method and apparatus for chemical imaging which is easy and inexpensive to operate relative to the available instrumentation for chemical imaging.

Yet another object of the present invention is to provide a method and apparatus for chemical imaging capable of operation in ambient conditions as opposed to vacuum based analysis techniques.

Another object of the present invention is to provide a method and apparatus for chemical imaging which requires minimal to no sample preparation as opposed to extensive sample preparation routines in vacuum based chemical analysis methods.

BRIEF SUMMARY OF THE INVENTION

The present invention involves the combination of scanning probe microscopy and laser induced breakdown spectroscopy to provide spatially resolved chemical analysis of the surface correlated with the surface topography. Topographical analysis is achieved by scanning a sharp probe across the sample at constant distance from the surface. Chemical analysis by the means of laser induced breakdown spectroscopy is achieved by delivering pulsed laser radiation to the sample surface through the same sharp probe, and consequent collection and analysis of emission spectra from plasma generated on the sample by the laser radiation.

The method of the present invention includes performing topographical scanning simultaneously with or followed by chemical analysis via scanning laser induce breakdown spectroscopy.

The apparatus of the present invention includes a scanning mechanism with a means of bringing a probe in the vicinity of a sample, probe, pulsed laser source, collection optics interfaced to an optical spectrometer, and electronics controlling the instrument.

The probe may be a solid fiber or a hollow pipette having a hollow tip. The probe may be coated with an opaque coating on the sides and having transparent face provided that the coating is durable enough to withstand the laser pulse delivered through the probe. If such coated probes are used then the operation of the instrument is similar to that of a near-field scanning probe microscope.

For uncoated probes, it is possible to create chemical sampling spot size on the order of the wavelength of laser radiation used for plasma generation. This determines spatial resolution of chemical imaging. For coated probes the analytical spot size may be smaller if the analysis is performed in the near field, i.e. at probe-sample separation smaller than the aperture of the transparent face of the probe. In this case the spatial resolution of chemical imaging will be determined by the size of the aperture, which can be several times smaller than the wavelength of laser light used for plasma generation. Unlike near field spectroscopy the preferred embodiment contemplates an uncoated probe so that light from all or most of the plasma plume can be received by the probe in those embodiments where the probe is also used as the receiving device. The emitted light from the plasma plume is characteristic of the material at the target site, which is spatially well defined. Therefore, unlike near field spectroscopy sensed light can be collected from the entire field of view without losing any spatial resolution of the chemical analysis.

This analytical method is very attractive because of its simplicity, speed, affordability with virtually no requirement for sample preparation if the study is conducted under ambient conditions. Combination of LIBS and scanning probe microscopy delivers a simple and elegant way to achieve chemical contrast to complement topographical studies performed by SPM.

More specifically, the invention comprises an apparatus for performing chemical and topographical analysis of a sample. The apparatus comprises a probe proximal to the sample, and a scanner coupled to the sample or probe for scanning the probe relative to the sample. A pulsed laser is optically coupled to the probe. A light collector receives light from the sample. An optical spectrometer is optically coupled to the light collector. A controller coupled to the scanner, laser and spectrometer controls the operation of the scanner, laser and spectrometer in a correlated, coordinated or synchronized fashion. The probe and scanner are used for topographical profiling the sample. The probe also is used for laser radiation delivery to the sample for generating a plasma plume from the sample. Optical emission from the plasma plume is collected by the light collector and delivered to the optical spectrometer. Analysis of emission spectrum by the optical spectrometer allows for identification of chemical composition of the sample at user selected sites.

In one embodiment the probe comprises a tapered end of an optical fiber. An opposing end of the optical fiber is coupled to the pulsed laser. In another embodiment the probe comprises a drawn microcapillary having a sub-micron size diameter and a distal end. The laser light is coupled into the probe by focusing the laser beam onto an optical fiber disposed in the distal end of the capillary. In this case the probe comprises an optical fiber and a drawn microcapillary having a sub-micron size diameter and a distal end. The laser light is coupled into the probe by coupling the light into the optical fiber. The optical fiber is disposed into the distal end of the capillary.

The scanner is a linearized scanner providing precise relative positioning of the probe and sample within a range of 1000×1000 micrometers. In this manner positioning of the probe for topological measurement and for chemical analysis at a selected site can be accurately made at different times.

In one embodiment the collector is comprised of a lens which collects the emitted light from the plasma plume created by the laser pulse. The emitted light then is delivered to the optical spectrometer. The apparatus may further comprise a mirror and the emitted light is delivered to the optical spectrometer by means of the mirror.

Alternatively, the apparatus further comprises a lens and an optic fiber. The emitted light is delivered to the optical spectrometer by means of direct imaging through a lens and optic fiber.

Still further apparatus further comprises an optical fiber and the emitted light is delivered to the optical spectrometer by means of the optical fiber.

In one embodiment the probe comprises a probe tip and an optical delivery path coupling the laser to the probe tip. The emitted light is collected by the same probe tip used for delivery of the laser pulse. The emitted light enters the probe tip and propagates along the optical delivery path in a direction opposite to delivery of light to the probe tip from the laser. The emitted light is delivered to the spectrometer.

The emitted light may be delivered to the spectrometer by means of a free space beamsplitter in the optical delivery path, or by means of a directional fiber coupler in the optical delivery path.

The invention is also characterized as a method for analyzing a material content and topography of a sample comprising the steps of performing topographical analysis of the sample by bringing a probe into a distance feedback relationship with the sample. The probe scans across the sample while maintaining constant separation between the probe and the sample. A scanned topological site on the sample is selected. Laser pulses are emitted from a pulsed laser. The laser pulses are coupled into an optical fiber. The laser pulses are delivered to the scanned topological site on the sample by means of the probe. A plasma is generated at the scanned topological site. A spectrum of optical emission from the plasma is measured. Specific chemical constituents are detected by analyzing line features of the collected spectrum.

The step of generating a plasma from the scanned topological site generates the plasma from the scanned topological site which is in the range of approximately 10 nm–2 $\mu$m diameter. The step of emitting laser pulses from a pulsed laser emits pulses with a pulse length from about 1 attosecond to about 1000 femtoseconds in duration.

The step of scanning the probe across the sample is in the form of a raster of pixels. A chemical analysis comprises generating a plasma from the scanned topological site, measuring a spectrum of optical emission from the plasma, and detecting specific chemical constituents by analyzing line features of the collected spectrum is performed in each pixel of the raster. The chemical composition of the sample is recorded for each pixel of the raster and a chemical map of the sample is produced. The measurement of the spectrum of optical emission from the plasma is performed after or acquired with a variable time delay of 100 ns–5 microseconds after delivering said laser pulses.

Although the method have been grammatically described above for the sake of ease in terms of steps it is to be expressly understood that the claimed invention is not limited by the "means" or "steps" restrictions of 35 USC 112. The invention having been briefly summarized, can now be better visualized by turning to the following drawings wherein like elements are reference by like numerals.

BRIEF DESCRIPTION OF THE DRAWINGS

FIG. 9b is a plan view of micrograph showing an AFM scan line taken across the crater of FIG. 9a.

FIG. 10b is a plan view of micrograph showing an AFM scan line taken across the crater of FIG. 10a.

The invention and its various embodiments can better be understood by now turning to the detailed description of the preferred embodiments.

DETAILED DESCRIPTION OF THE PREFERRED EMBODIMENTS

The method comprises performing microtopographical analysis of the sample with a scanning probe, selecting a scanned topological site on the sample, generating a plasma plume at the selected scanned topological site, and measuring a spectrum of optical emission from the plasma at the selected scanned topological site.

The apparatus comprises a scanning probe, a pulsed laser optically coupled to the probe, an optical spectrometer, and a controller coupled to the scanner, laser and spectrometer for controlling the operation of the scanner, laser and spectrometer. The probe and scanner are used for topographical profiling the sample. The probe is also used for laser radiation delivery to the sample for generating a plasma plume from the sample. Optical emission from the plasma plume is collected and delivered to the optical spectrometer so that analysis of emission spectrum by the optical spectrometer allows for identification of chemical composition of the sample at user selected sites.

Figure 1:
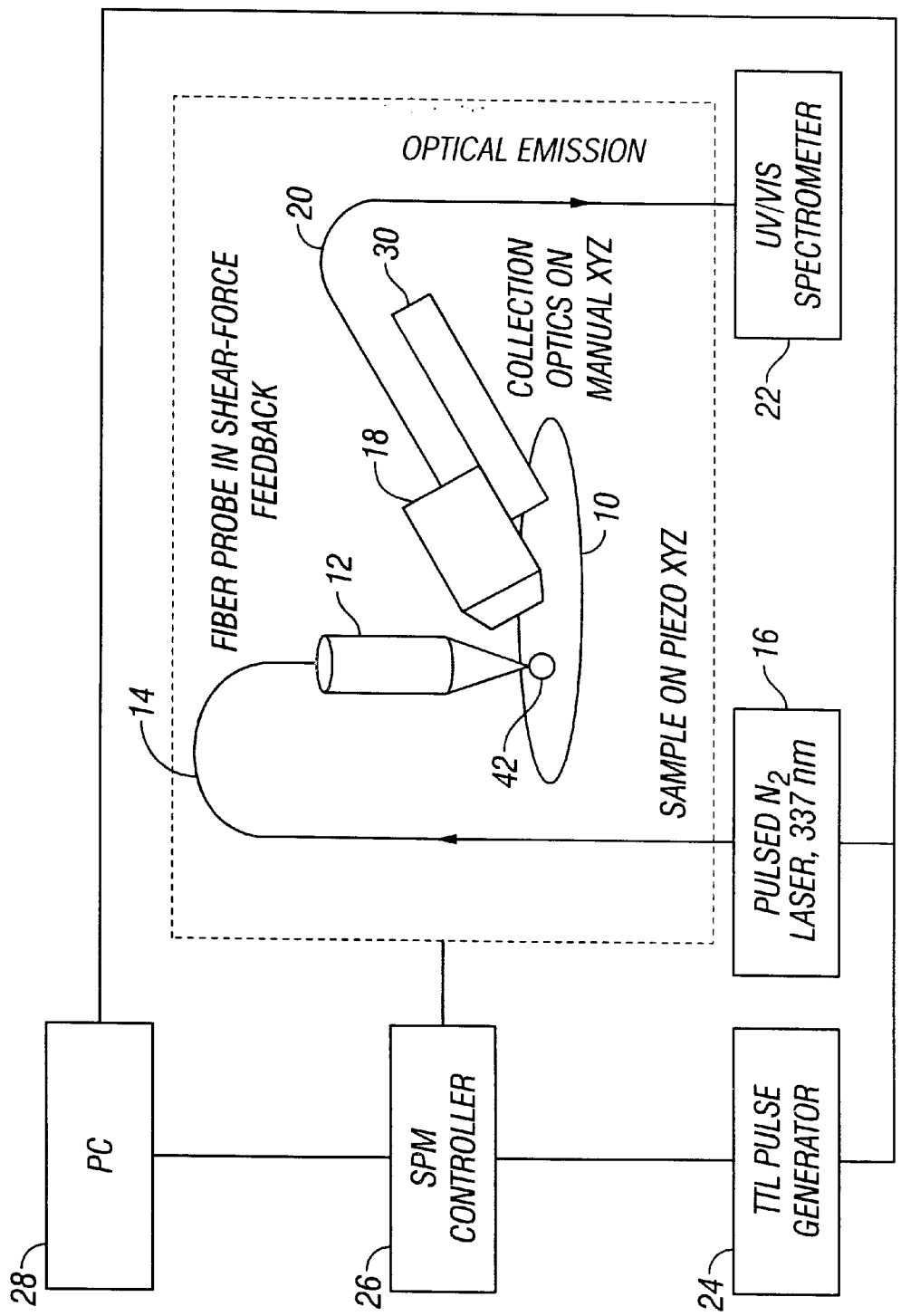
FIG. 1 is a block diagram of the SPPA instrument of the invention showing its principal components.

In order to achieve spatially resolved chemical imaging, LIBS is combined with a shear-force fiber probe SPM in a single instrument which we refer to as scanning probe plasma analyzer, SPPA. A block diagram of the instrument is shown in FIG. 1. The instrument of FIG. 1 demonstrates the feasibility of the method and apparatus. It is to be expressly understood that the apparatus may take on many other forms different from that shown in FIG. 1 without departing from the scope and teachings of the invention. A fiber probe 12 in shear-force feedback with a sample 10 as described below it scanned relative to sample 10. Laser light is provided to probe 12 by means of optic fiber 14 from a laser 16, which is shown by way of example in FIG. 1 as a pulsed $N_2$ laser tuned at 337 nm such as model VSL-337ND manufactured by Laser Science, Inc. of Franklin, Mass. Laser 16 in the illustrated embodiment provides a pulse with a power density of $10^9$ W/cm$^2$ with a pulse period of 1–3 ns at 20 Hz with a total energy dose to the site of the order of 250 $\mu$J. It is to be expressly understood that other optical sources and couplings can be readily substituted. Light emitted from the plasma ball created by the interaction of the laser light and sample 10 is collected by optical collector 18 and coupled by means of optic fiber 20 to a ultra violet and visible (UV/VIS) spectrometer 22 such as model S2000 manufactured by Ocean Optics Inc. of Dunedin, Fla. Collector 18, which is a generic 20×microscope objective, is mounted on an xyz micromanipulator 30 and thus can be positioned to focus on and track the spot of the plasma ball created by laser 16 as it scans sample 10. Laser 16 and spectrometer 22 are synchronized by means of a TTL pulse generator such as model 75 manufactured by Wavetek of San Diego, Calif., which in turn is controlled by an SPM controller 26 such as model Pscan2 manufactured by Pacific Scanning Corp. of Pasadena, Calif., which is also coupled to the mechanical stage on which sample 10 is mounted. Personal computer 28 is coupled to both controller 26 and to spectrometer 22 for coordinated data input and control.

Probes 12 can be made by tapering an optical fiber to a sharp point or by thermomechanical drawing of a micropipette. Fiber tapering can be achieved by conventional chemical etchings or by thermo-mechanical drawing, as described by Betzig, Appl. Phys. Lett. 60 (1992) 2484–2486. Typical end radius of curvature of the probes is below 200 nm.

Shear force feedback is used for maintaining probe 12 at the constant separation from sample 10. This method is based on monitoring of mechanical oscillations of probe 12 excited by an external vibration source such as a piezoelectric transducer mechanically coupled either to probe 12 or sample 10. Such oscillations are damped when probe 12 is brought sufficiently close to sample 10, usually closer than 10 nm. Monitoring the changes in the oscillation parameters of probe 12, such as oscillation amplitude and phase, provides the means for controlling the separation between sample 10 and probe 12 and keeping the separation constant. Such a conventional method of positioning feedback was developed for early developments in the NSOM field.

The feedback for SPPA may be implemented by using any variation of the shear force method reported in the literature. Originally, Betzig implemented optical schemes: such as a separate laser for illuminating the apex of probe 12 from the side. The shadow formed by the tip of probe 12 was projected onto a split photodiode positioned behind the probe. The phase and amplitude of the diode output are to those of the probe's oscillation. Another family of shear force detection uses non-optical detection. Hsu has developed an impedance measurement based methods as described in Rev. Sci. Instrum. 66 (1995) 3177–3181. Karrai has suggested the use of piezoelectric tuning forks as detectors. See, Karrai et.al. Appl. Phys. Lett., 66 (1965) 1842–1844. Debarre et al. Rev. Sci. Instr. 68 (1997) 4120–4123 describes the use of piezoelectric membranes for shear force detections. Any of these conventional feedback methods now known or later devised may be used for controlling the separation of probe 12 and sample 10.

After probe 12 is brought into a controlled distance from sample 10 with feedback, the scanning is performed by rastering probe 12 across sample 10, or sample 10 across probe 12. It preferable to use a highly linear scanning system which allows accurate registration of probe position relative to sample 10. Utilization of a linearized scanning system allows for reliable probe positioning on the topographical landscape for the purposes of chemical analysis of specific topographical features. If no linearization is implemented, then there is little possibility to perform chemical analysis of features "on demand", i.e. bringing the probe at specific locations of interest which are later selected by user on the basis of acquired topographical data.

Figure 2A:
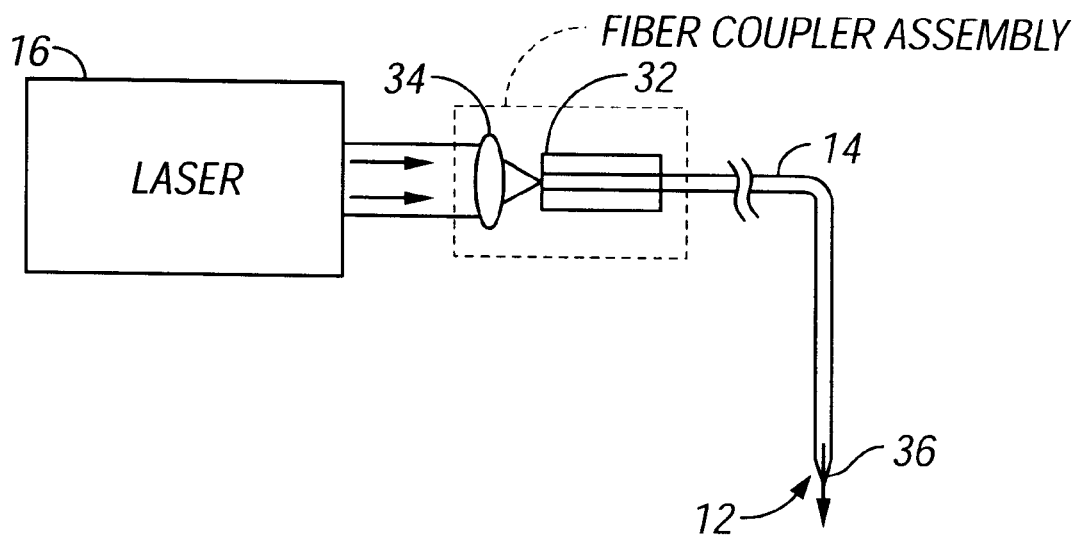
FIG. 2a is a diagram illustrating a sharp probe using a tapered optical fiber.
Figure 2B:
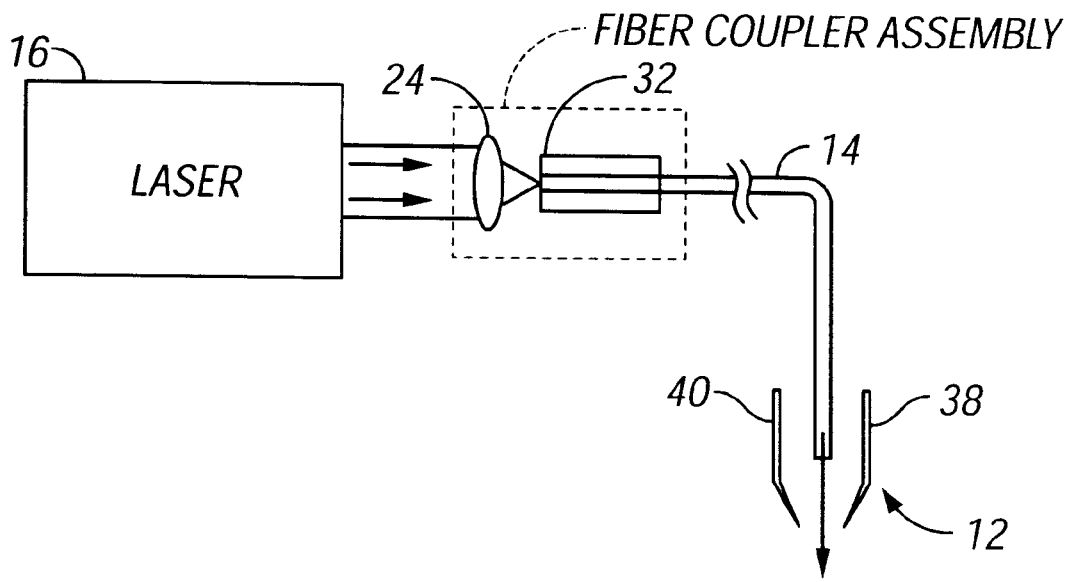
FIG. 2b is a diagram illustrating a sharp probe using a tapered micropipette.

An important part of the method is delivery of the pulsed optical radiation to sharp probe 12. Details of light coupling into probe 12 depend on the type of probe 12 utilized. If a sharp optical fiber probe 12 is used as diagrammatically depicted in FIG. 2a, then the light is coupled through collection optics 34 into the distal end 34 of the same fiber 14 which comprises probe 12, on the proximal end of which probe tip 36 is formed. In the case of hollow pipette probe 12 the light is delivered inside pipette 38 either by means of an optical fiber 14 inserted into pipette 38 as diagrammatically depicted in FIG. 2b, or by focusing the laser beam on the distal end 40 of pipette 38 (not shown).

When a sufficient amount of laser power is delivered to sample 10, a hot plasma plume 42 is formed from the material of sample 10. Plume 42 emits light the spectrum of which is characteristic of chemical composition of sample 10. Typically plume 42 persist for the order of one or a few ps whereas the pulse from laser 16 may be 1–3 ns long. Part of this plasma emission is captured by light collection optics 18 and delivered to spectrograph 22 where the light is wavelength dispersed and the spectrum is recorded. The presence of characteristic emission lines in the spectrum allows to determine the presence of specific elements and molecules.

Figure 3A:
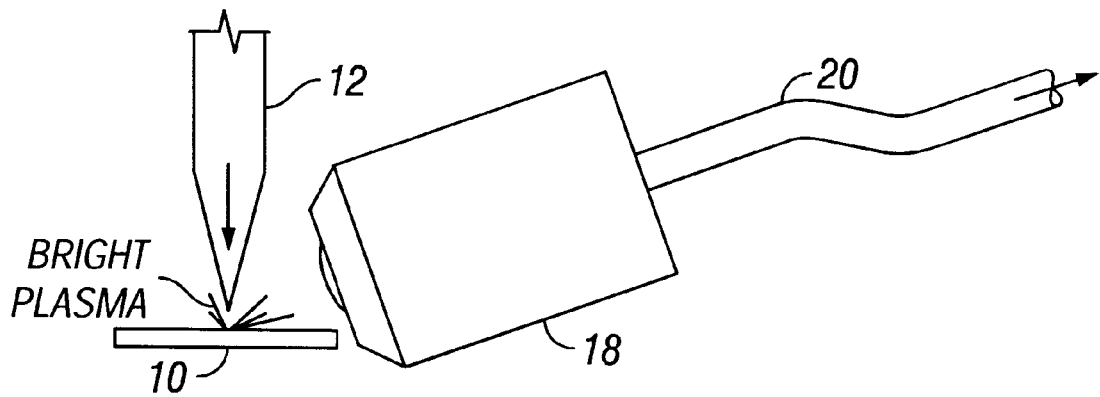
FIG. 3a is a diagram showing collection of light from the plasma plume created by the laser through a lens and optical fiber combination.

In one embodiment collection of the optical emission is accomplished by a lens 18 which images the plasma plume 42 on a face of an optical fiber 20, which in turn guides the light to spectrograph 22 as illustrated in FIG. 3a.

Figure 3B:
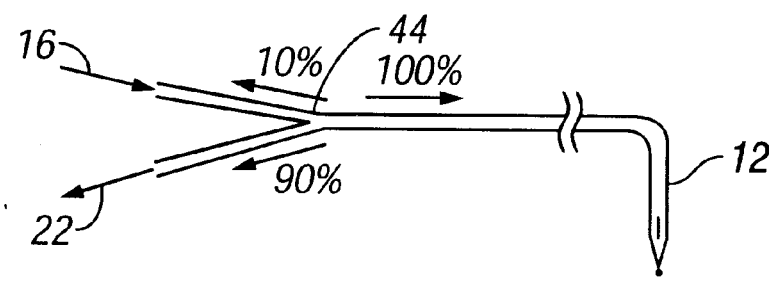
FIG. 3b is a diagram showing collection of light from the plasma plume created by the laser through a directional fiber optical splitter.
Figure 3C:
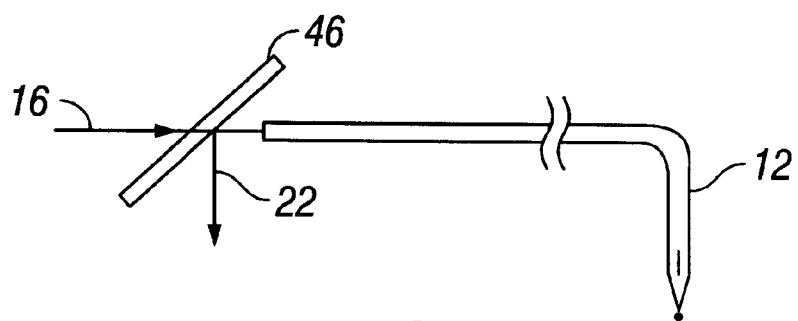
FIG. 3c is a diagram showing collection of light from the plasma plume created by the laser using a free space beamsplitter.

Some fraction of the emitted light enters probe 12 that delivered the light to the surface of sample 10, propagates along the path of the primary laser pulse although in the reverse direction. This effect is used in another embodiment of light collection where this back propagating light is delivered to spectrograph 22 by the means of a directional fiber optical splitter 44 illustrated in FIG. 3b or a free space beamsplitter or mirror 46 illustrated in FIG. 3c. This embodiment provides a particularly simple way to collect the emitted light as no special collection optics is involved, and consequently no alignment is needed.

The apparatus of the invention now having been generally described consider the methodology of its use. The experimental approach embodies the following steps.

1. Topographical analysis: A sharp optical probe 12 is brought into shear force feedback to maintain probe-sample separation and scanned at constant distance from the surface of sample 10 to examine the sample topography. No laser radiation is used in this analysis.

2. Chemical analysis: After features of interest are located in the topographical image, probe 12 is positioned and LIBS data recorded to provide chemical information to further characterize sample 10. When specific chemical signatures are observed, they can be monitored during a rescan of the surface to generate a spatially resolved image of the identified species.

The method may be conducted in ambient conditions as well as in a controlled atmosphere or vacuum chamber. There are no specific requirements for sample preparation for LIBS studies. For topographical analysis, the sample should be flat enough to accommodate the specific requirements of the scanning system employed.

Interaction of the laser radiation with sample 10 and formation of the plasma plume 42 damages sample 10. A crater is usually formed in a location where the light pulse is delivered. Such cratering should be minimized in order to achieve best possible resolution of chemical imaging. Crater size is decreased by controlling the amount of laser radiation delivered to sample 10. This can be done by attenuating the laser beam before it enters optical fiber 14 used for light delivery to probe 12.

Reduction of laser power leads to a decreased amount plasma produced and subsequently to decreased LIBS signal. High sensitivity detectors are used in spectrograph 22 to record the spectra from such weak LIBS events. Typically, a cooled CCD detector is used for spectrum recording. Careful timing of LIBS signal acquisition also helps to improve signal-to-noise ratio (SNR) in LIBS spectra. It is well established that the signal to noise ratio (SNR) can be greatly improved by time delayed collection of LIBS signals. In this approach there is a time delay between the onset of plasma plume formation and the beginning of spectrum a cquisition. The delay typically ranges from several hundreds of nanoseconds to several microseconds depending on the type of laser used for generating plasma 42. During the delay time, initially the hot plasma 42 cools down, and the continuous spectral background due to Bremsstrahlung processes is significantly reduced. This background would typically mask weaker atomic and molecular emissions which are present in the emission spectrum on later stages of plasma plume development.

The delay is typically realized in hardware by using gated intensified CCD detectors or sufficiently fast gateable CCD detectors. In both cases the detector timing is synchronized with that of the laser pulse as illustrated in FIG. 1.

It is possible that probe will become contaminated by the constituents from plasma plume 42 during the instrument operation. Probe contamination may reduce light transmission efficiency of probe 12 and introduce artifacts in the chemical analysis. In one embodiment probe 12 can be cleaned by retracting probe 12 from sample 10 and then delivering a train of high power laser pulses through probe 12. Such pulses remove the contaminants from probe 12 and effectively clean probe 12.

Consider now a comparison of focused beam and fiber probe LIBS signals. A necessary test for the SPPA concept is to demonstrate that laser pulses delivered to sample 10 through a tapered fiber optic probe 12 in position feedback can produce usable signals without damaging probe 12. To compare LIBS and SPPA we have used a specimen of Murchison meteorite as a test sample. This meteorite which fell at Murchison, 80 km north of Melbourne, on the Sep. 29, 1969, is widely studied and its composition is well known. The majority of this carbonaceous meteorite is composed of iron, silicon and magnesium oxides with inclusions of aluminum, sodium and potassium oxides as well as organic molecules including amino-acids.

Figure 4:
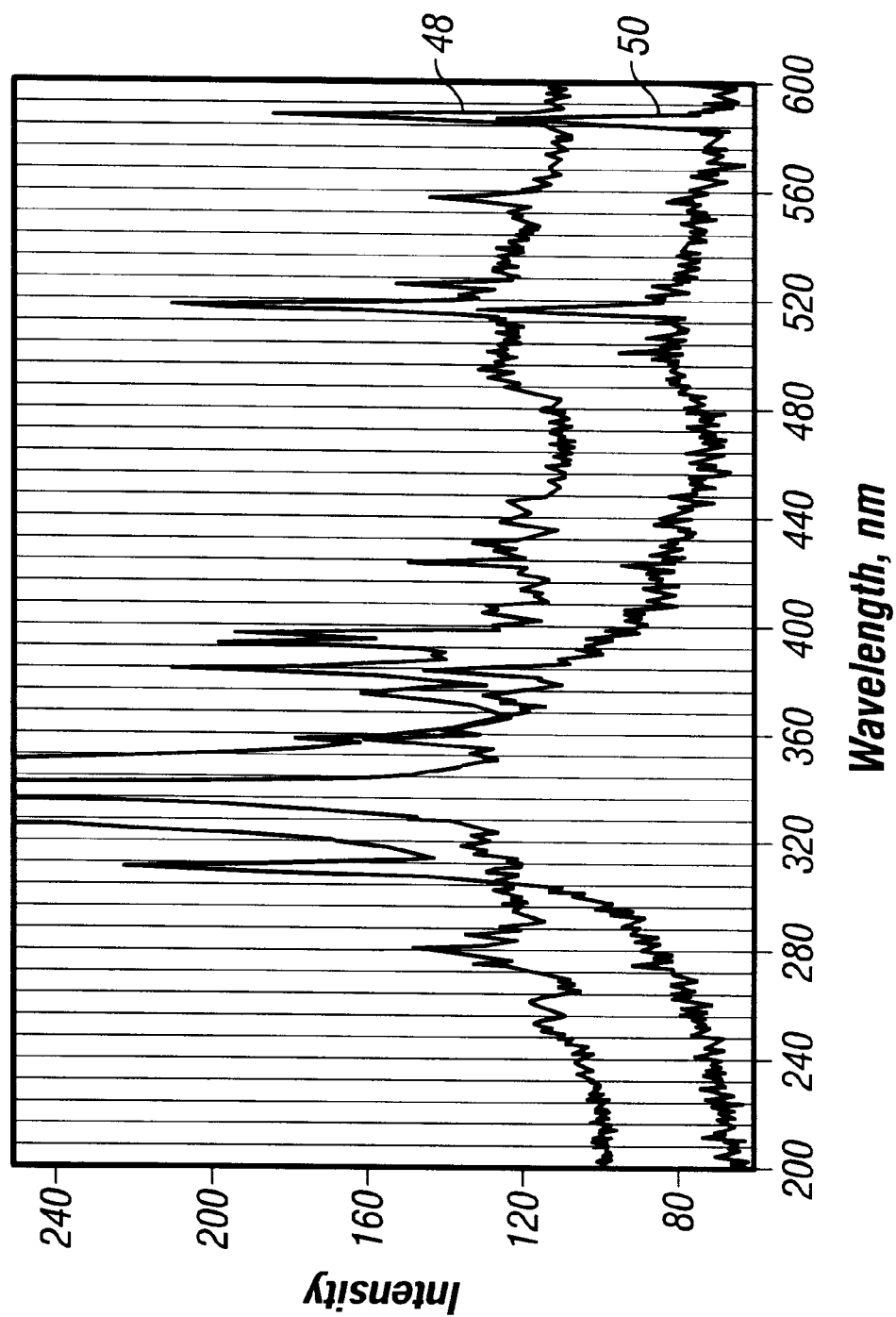
FIG. 4 is a graph comparing the intensity of a LIBS spectra signal from the same sample from a focussed beam laser and from a probe according to the invention.

FIG. 4 shows a comparison of LIBS signals excited by a single laser pulse delivered to the sample by focusing the laser beam as depicted by line 48 and by feeding the beam through a fiber probe 12 on position feedback as depicted by line 50. The most notable and exciting feature of the spectrum with probe 12 is that it is not much different from that with a focused beam in terms of signal intensity and signal-to-noise ratio. The two spectra were acquired in different locations of the same meteorite sample, which explains the variability in presence or absence of specific spectral features in particular spectrum.

Figure 5:
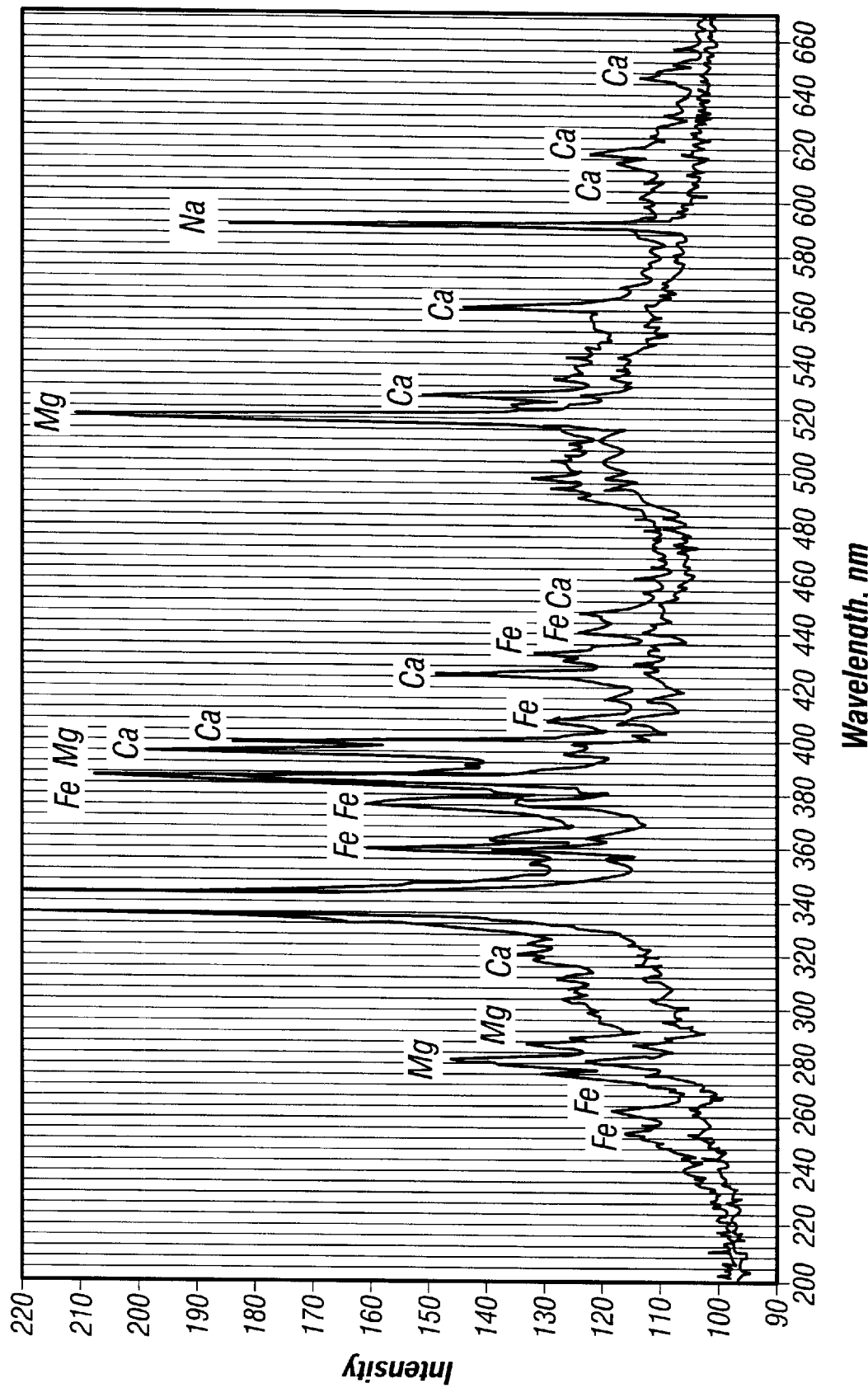
FIG. 5 is a graph of two spectra generated by single laser pulses applied according to the invention in two different locations on the sample.

LIBS spectra of the Murchison meteorite characterize the local chemical composition of the sample. FIG. 5 shows two spectra generated by single laser pulses in two different locations on the sample. Known components of the meteorite are observed in the spectra, including iron, magnesium, calcium and sodium. Aluminum and silicon (which are present in form of oxides) and carbon from amino acids are not observed. This is probably because aluminum oxide is a minor constituent of the meteorite, while detection of carbon and silicon in LIBS requires higher performance spectrometers. The analysis of spectral features shows similar metal content in both locations. However, one location is clearly enriched in calcium relative to another.

In order to investigate a material with known chemical composition and different chemical phases, a sample of basaltic rock was also prepared. Basaltic rock is a metamorphic rock which is highly inhomogeneous with feature size ranging from tens of microns down to a fraction of a micron. Major phases and their chemical composition of a typical basalt are listed in Table 1.

TABLE 1

Composition of Basaltic Rock

| Phase | Chemical Composition |
| --- | --- |
| Olivine | $(Mg_{0.9}{}^{++}Fe_{0.1}{}^{++})_2SiO_4$ |
| Plagioclase Feldspar | $(Ca_{1-x}Na_x)Al_{2+x}Si_{2+x}O_8$ |
| Magnetite | $Fe_3O_4$ |
| Pyroxene | $Ca(Mg,Fe)Si_2O_6$ |
| Glass | 60–70% silica with MgO, FeO and others |
| Titanium containing phase | TiO |

A chip was broken off the bulk rock and polished with a progression of abrasive materials down to 1 micron finish. At this roughness the surface has a mirror look. When observed in a reflective light microscope, a variety of regions with different grayscale shades are observed. Reflective microscopy is commonly used in mineralogy, and it is known that each grayscale shade corresponds to a chemically different phase.

Figure 6A:
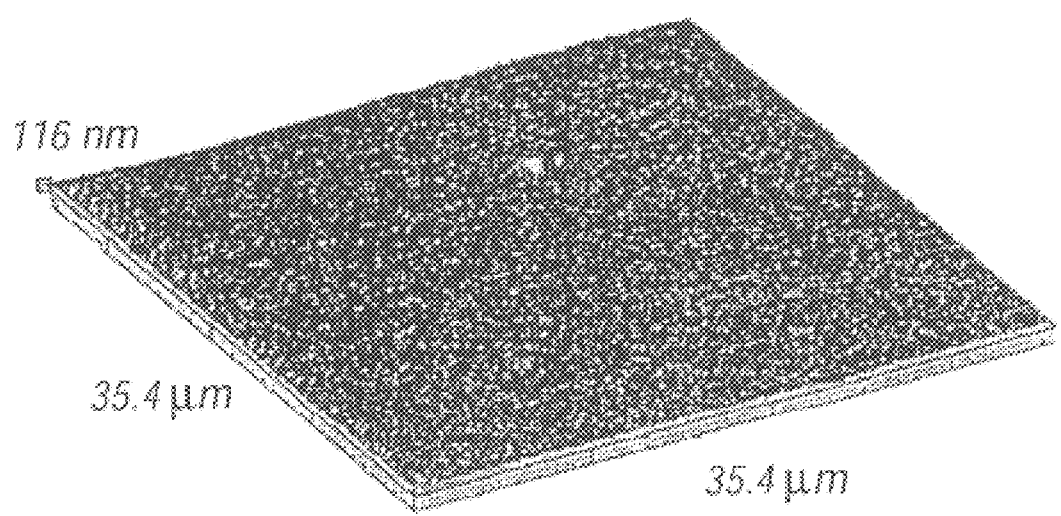
FIGS. 6a and 6b are micrographs showing two different surface areas of a basaltic rock sample.
Figure 6B:
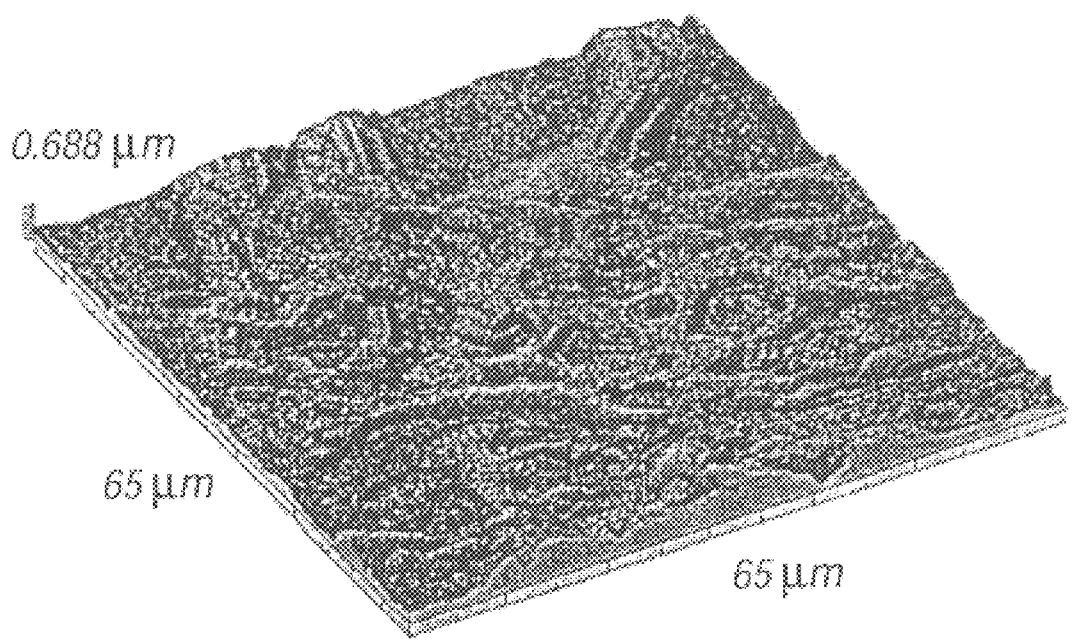

After polishing, the chip was glued on a small magnetic disk and placed on the SPPA scanner of the invention as shown in FIG. 1. Examples of topographical scans are shown in FIGS. 6a and 6b. A relatively flat area fills the depiction shown in FIG. 6a is probably a large domain of a single phase. However, FIG. 6b shows a topologically richer landscape with features on various scales. This relief was probably formed by interaction of abrasive material with different phases of the rock. The hardness of a phase depends on its chemical composition, so softer phases exhibit more depression after polishing compared to harder ones.

Figure 7A:
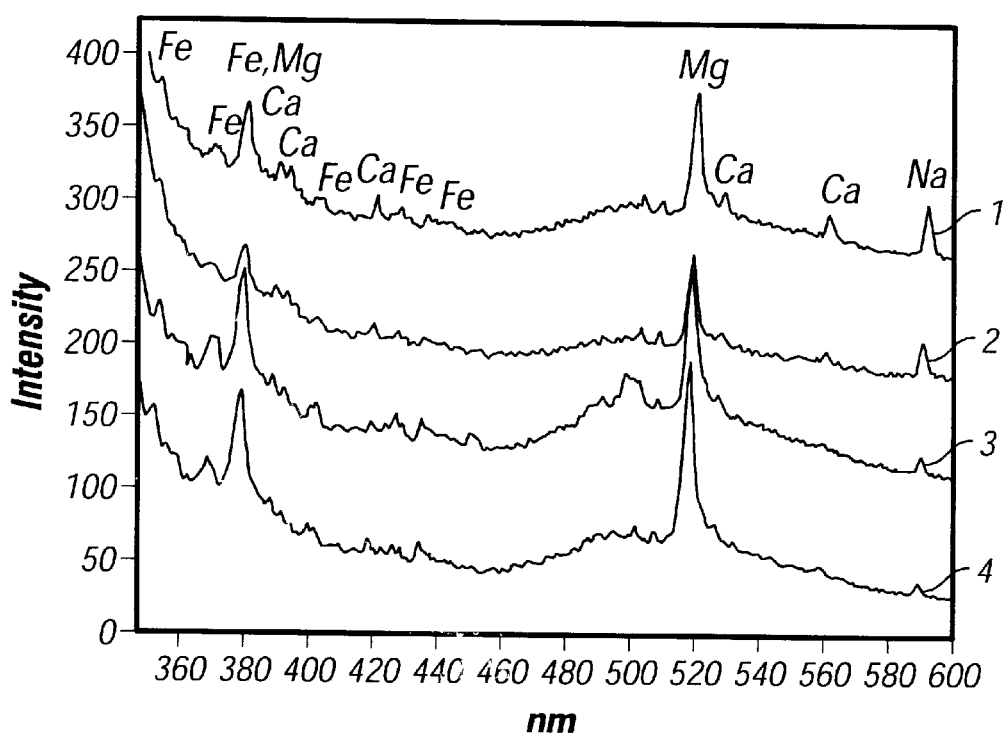
FIGS. 7a and 7b are graphs of four spectra obtained at four different locations of the basaltic rock sample of FIGS. 6a and 6b over different wavelength domains of the spectra.
Figure 7B:
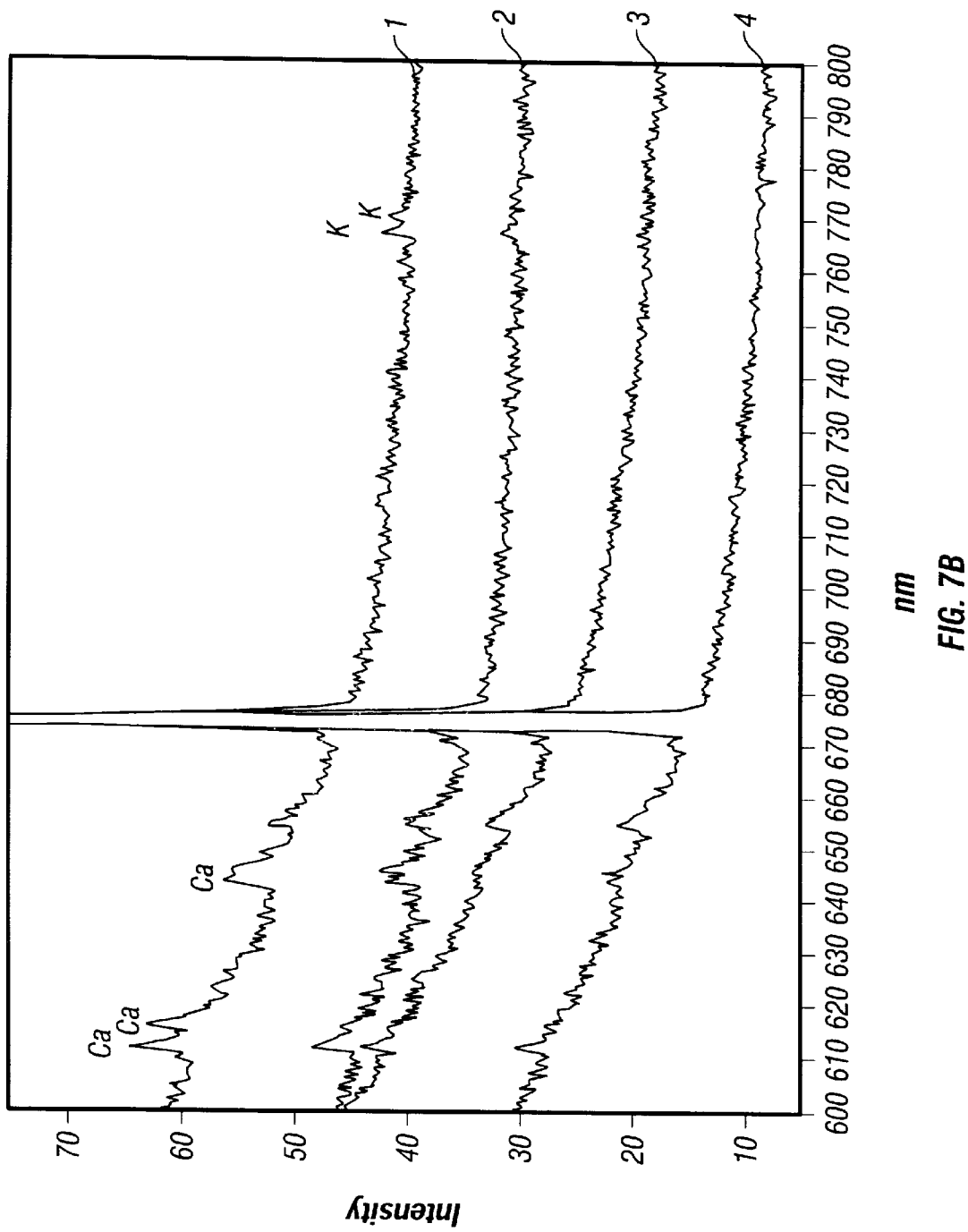

After topographical analysis, chemical analysis of the same sample performed. FIGS. 7a and 7b each show four LIBS spectra acquired with different probe locations on the same sample 10. Each spectrum is generated with a single laser pulse with no attenuation of the laser beam. The spectra are noticeably different. In particular, spectrum #2 shows approximate 3:1 calcium and potassium enrichment relative to spectrum #1. The ratios were calculated after normalizing the data on the total spectral intensity, subtracting local background and then comparing the peak values for spectral features corresponding to particular elements.

Figure 8:
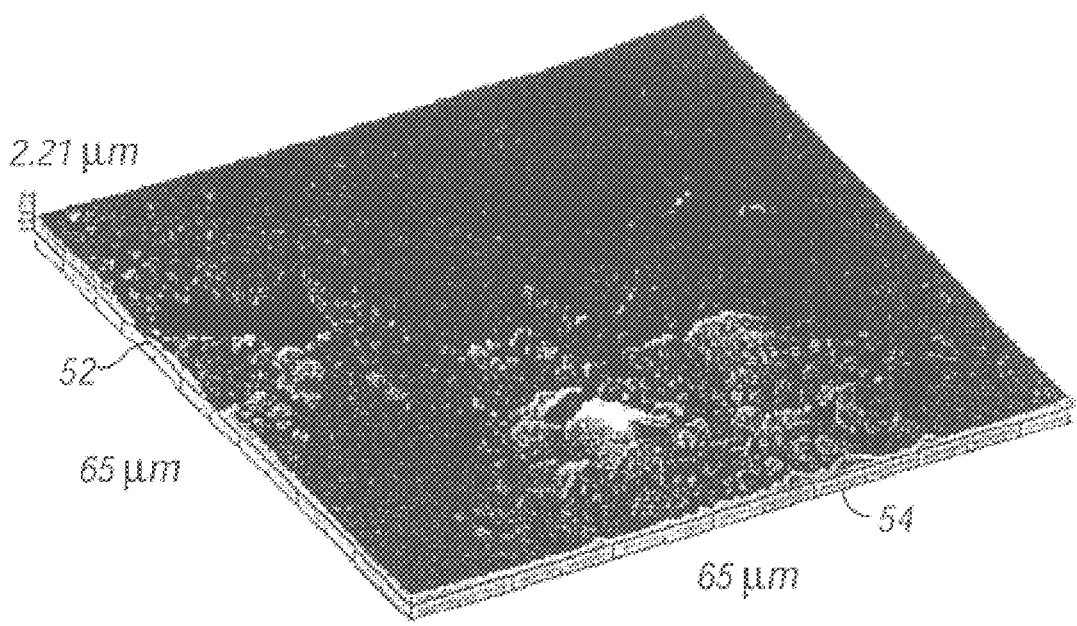
FIG. 8 is a micrograph of two locations showing the surface deformation caused by the laser pulse.

As was discussed above, the SPPA method is inherently destructive. The topological spot which is measured and selected is later vaporized in part by the laser pulse. Pulsed laser radiation delivered to sample 10 through probe 12 creates craters in the sampling area and changes microtopography. High laser powers generate bright plasmas which are easier to analyze, however the amount of damage is unacceptably high. FIG. 8 shows two locations 52 and 54 of surface deformation. At each location 52 and 54 maximum amount of laser power coupled into fiber 14 was delivered to sample 10. In both cases the damage is on the order of tens of microns.

Figure 9A:
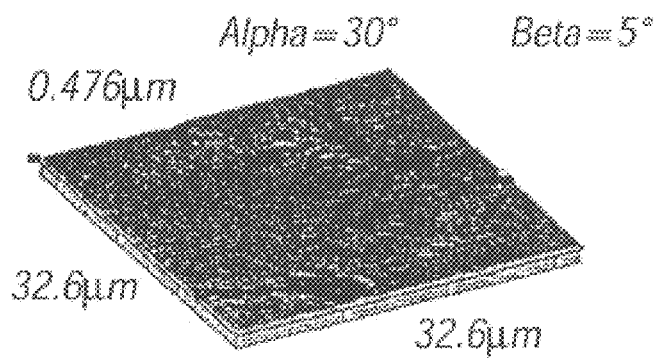
FIG. 9a is a perspective view of a micrograph of a sample area at an initial laser power level.
Figure 9B:
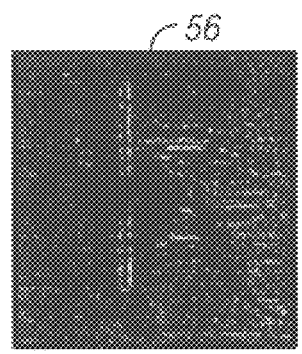
Figure 9C:
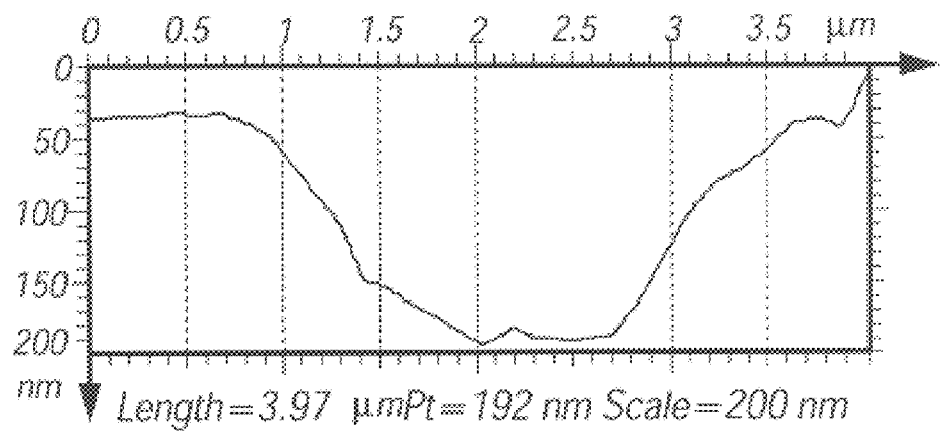
FIG. 9c is a graph of the topological data output or measured topological profile of the crater shown in FIGS. 9a and 9b.
Figure 10A:
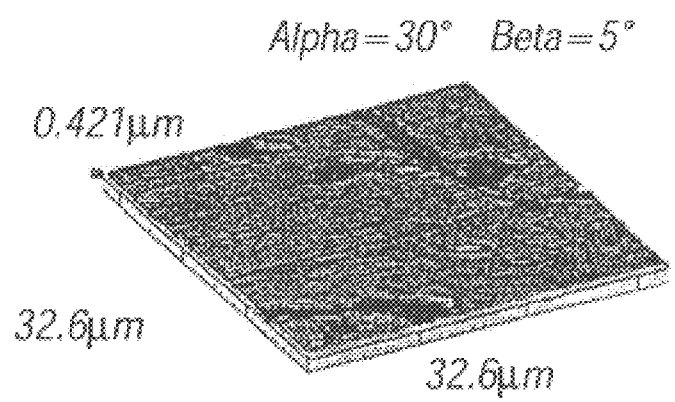
FIG. 10a is a perspective view of a micrograph of a sample area at a reduced laser power level.
Figure 10B:
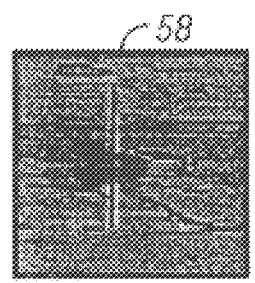
Figure 10C:
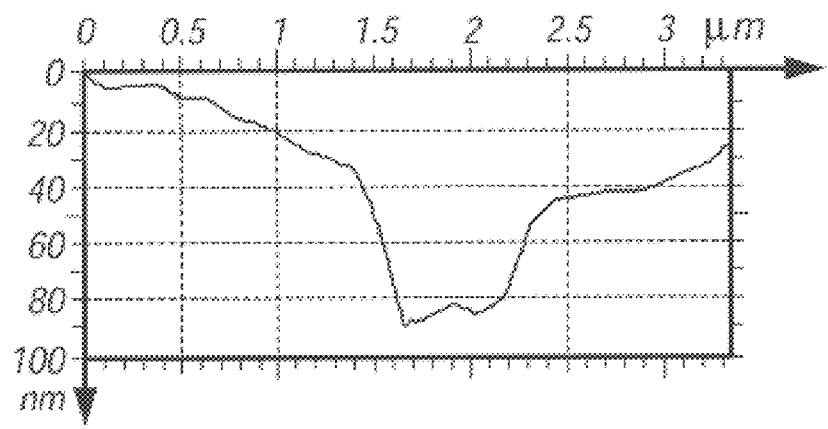
FIG. 10c is a graph of the topological data output or measured topological profile of the crater shown in FIGS. 10a and 10b.

The challenge is to minimize such damage while still producing a sufficiently high optical signal. Reduction of laser power per pulse leads to reduced crater size, as demonstrated in FIGS. 9a–9c and FIGS. 10a–10c. FIG. 9a is a micrograph of a sample area at an initial laser power level of 4 kW exiting the laser probe. At this power the LIBS spark is visible to the eye. An AFM scan is taken across the scan line 56 of the crater as shown in the plan view of FIG. 9b. The data output or measured topological profile of the crater is shown in FIG. 9c. The laser beam was then attenuated by an iris before entering fiber optic 14 to a power level when the plasma plume is no longer visible to the eye. FIG. 10a is a micrograph of a sample area at the reduced laser power level. An AFM scan is taken across the scan line 58 of the crater created at the reduced power level as shown in the plan view of FIG. 10b. The data output or measured topological profile of the crater is shown in FIG. 10c. By using lower laser power crater-size is reduced from several tens of microns to sub-micron dimensions. The crater is substantially shallower and smaller in diameter.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for performing chemical and topographical analysis of a sample comprising:
   a probe proximal to said sample;
   a scanner coupled to said sample or probe for scanning said probe relative to said sample;
   a pulsed laser optically coupled to said probe;
   a light collector receiving light from said sample;
   an optical spectrometer optically coupled to said light collector;
   a controller coupled to said scanner, laser and spectrometer for controlling the operation of said scanner, laser and spectrometer, said probe and scanner being used for topographical profiling said sample, said probe also being used for laser radiation delivery to said sample for generating a plasma plume from said sample; optical emission from said plasma plume being collected by said light collector and delivered to said optical spectrometer, analysis of emission spectrum by said optical spectrometer allowing for identification of chemical composition of said sample at user selected sites.

2. The apparatus of claim 1 wherein said probe comprises a tapered end of an optical fiber, an opposing end of said optical fiber being coupled to said pulsed laser.

3. The apparatus of claim 1 wherein said probe comprises a drawn microcapillary having a sub-micron size diameter and a distal end, said laser light being coupled into said probe by focusing said laser beam onto said distal end of said capillary.

4. The apparatus of claim 1 wherein said probe comprises an optical fiber and a drawn microcapillary having a sub-micron size diameter and a distal end, said laser light being coupled into said probe by coupling said light into said optical fiber, said optical fiber being disposed into said distal end of said capillary.

5. The apparatus of claim 1 wherein said scanner is a linearized scanner providing precise relative positioning of said probe and sample within a range of 1000×1000 micrometers.

6. The apparatus of claim 1 wherein said collector is comprised of a lens which collects said emitted light from said plasma plume created by said laser pulse, said emitted light then being delivered to said optical spectrometer.

7. The apparatus of claim 6 further comprising a mirror and wherein said emitted light is delivered to said optical spectrometer by means of said mirror.

8. The apparatus of claim 6 further comprising a lens and optic fiber and wherein said emitted light is delivered to said optical spectrometer by means of direct imaging through a lens and optic fiber.

9. The apparatus of claim 6 further comprising an optical fiber and wherein said emitted light is delivered to said optical spectrometer by means of an optical fiber.

10. The apparatus of claim 1 wherein said probe comprises a probe tip and an optical delivery path coupling said laser to said probe tip and wherein said emitted light is collected by said same probe tip used for delivery of said laser pulse, said emitted light entering said probe tip and propagating along said optical delivery path in a direction opposite to delivery of light to said probe tip, from said laser, said emitted light being delivered to said spectrometer.

11. The apparatus of claim 10 wherein said emitted light is delivered to said spectrometer by means of a free space beamsplitter in said optical delivery path.

12. The apparatus of claim 10 wherein said emitted light is delivered to said spectrometer by means of a directional fiber coupler in said optical delivery path.

13. A method for analyzing a material content and topography of a sample comprising:
   performing topographical analysis of said sample by bringing a probe into a distance feedback relationship with said sample;
   scanning said probe across said sample while maintaining constant separation between said probe and said sample;
   selecting a scanned topological site on said sample;
   emitting laser pulses from a pulsed laser;
   coupling said laser pulses into an optical fiber;
   delivering said laser pulses to said scanned topological site on said sample by means of said probe;
   generating a plasma from said scanned topological site;
   measuring a spectrum of optical emission from said plasma; and
   detecting specific chemical constituents by analyzing line features of said collected spectrum.

14. The method of claim 13 wherein generating a plasma from said scanned topological site generates said plasma from said scanned topological site which is in the range of approximately 10 nm–2 $\mu$m diameter.

15. The method of claim 13 wherein emitting laser pulses from a pulsed laser emits pulses with a pulse length from about 1 attosecond to about 1000 femtoseconds in duration.

16. The method of claim 15 wherein generating a plasma from said scanned topological site generates said plasma from said scanned topological site which is in the range of approximately 10 nm–2 $\mu$m diameter.

17. The method of claim 13 wherein scanning said probe across said sample is in the form of a raster of pixels and where a chemical analysis comprised of generating a plasma from said scanned topological site, measuring a spectrum of optical emission from said plasma, and detecting specific chemical constituents by analyzing line features of said collected spectrum, is performed in each pixel of said raster.

18. The method of claim 17 wherein measuring said spectrum of optical emission from said plasma is performed with a variable time delay of 100 ns–5 microseconds after delivering said laser pulses.

19. The method of claim 17 wherein said chemical composition of said sample is recorded for each pixel of said raster and a chemical map of said sample is produced.

20. A method for microanalyzing a material content and topography of a sample comprising:
   performing microtopographical analysis of said sample with a scanning probe;
   selecting a scanned topological site on said sample;
   generating a plasma plume at said selected scanned topological site; and
   measuring a spectrum of optical emission from said plasma at said selected scanned topological site.

21. An apparatus for performing chemical and topographical analysis of a sample comprising:
- a scanning probe;
- a scanner coupled to said scanning probe or adapted to be coupled to said sample for scanning said probe relative to said sample;
- a pulsed laser optically coupled to said probe;
- an optical spectrometer;
- a controller coupled to said scanner, laser and spectrometer for controlling the operation of said scanner, laser and spectrometer, said probe and scanner being used for topographical profiling said sample, said probe also being used for laser radiation delivery to said sample for generating a plasma plume from said sample; optical emission from said plasma plume being collected and delivered to said optical spectrometer so that analysis of emission spectrum by said optical spectrometer allows for identification of chemical composition of said sample at user selected sites.

* * * * *